United States Patent [19]

Warwel et al.

[11] Patent Number: 5,218,131
[45] Date of Patent: Jun. 8, 1993

[54] PROCESS FOR THE METATHESIS OF OLEFINS AND FUNCTIONALIZED OLEFINS

[75] Inventors: Siegfried Warwel, Aachen; Hans-Gerd Jägers, Gladbeck; Barbara Ercklentz, Mönchengladbach, all of Fed. Rep. of Germany

[73] Assignee: Huels Aktiengesellschaft, Marl, Fed. Rep. of Germany

[21] Appl. No.: 658,870

[22] Filed: Feb. 22, 1991

[30] Foreign Application Priority Data

Mar. 2, 1990 [DE] Fed. Rep. of Germany ....... 4006539

[51] Int. Cl.$^5$ ............................................. C11C 3/06
[52] U.S. Cl. ..................... 554/163; 554/162; 560/190; 585/525; 585/547; 502/202; 502/102; 502/241
[58] Field of Search ............. 260/403.5; 554/162, 554/163; 560/190; 585/525, 647; 502/102, 202, 241

[56] References Cited

PUBLICATIONS

Fel'dbyum et al, Zhurnal Organacheskoi Khimil, vol. 9, #5, pp. 870–874, 1973.
Xiaoding et al, Journal Molecular Catalyst, vol. 36(1–2) pp. 47–66, 1986.
Chemical Abstracts, vol. 79, #2, 1973, 66835p.
Xu et al, Chemical Abstracts, vol. 106, #15, p. 570, 1987, 119061t.

*Primary Examiner*—José G. Dees
*Assistant Examiner*—Deborah D. Carr
*Attorney, Agent, or Firm*—Oblon, Spivak, McClelland, Maier & Neustadt

[57] ABSTRACT

A process for the metathesis of olefins and functionalized olefins on $Re_2O_7/Al_2O_3$-containing catalysts, which comprises effecting metathesis reaction in the presence of one or more halogen-free organoaluminum compounds as activators.

14 Claims, No Drawings

PROCESS FOR THE METATHESIS OF OLEFINS AND FUNCTIONALIZED OLEFINS

BACKGROUND OF THE INVENTION

1. Field of the Invention

The present invention relates to a process for the metathesis of olefins and functionalized olefins on $Re_2O_7/Al_2O_3$-containing catalysts in which process activators are used.

2. Description of the Background

The metathesis of olefinic hydrocarbons is used in the manufacture of specific olefins, dienes and polyenes and unsaturated polymers. Even olefins with functional groups are subject to the metathesis reaction provided suitable catalysts are used. In so doing, of special importance is the metathesis of unsaturated fatty acid methyl esters, which are produced on a large scale by transesterifying native fats and oils with methanol and are thus commercially available as parent compounds. The metathesis of these esters opens a new and simple access to intermediate products through chemical engineering for the commercial production of surfactants, plastics, plasticizers, lubricants and a whole range of fine chemicals.

Warwel, Erdol-Erdgas-Kohle, Petroleum, Natural Gas, Coal, Vol. 103 (1987), pp. 238–45, describes industrial metathesis procedures, wherein predominantly $Re_2O_7/Al_2O_3$-, $CoO-MoO_3/Al_2O_3$ and $WO_3/SiO_2$ catalysts are used. According thereto, only the $Re_2O_7/Al_2O_3$ catalyst is already active at room temperature. Generally, tin alkyls are added as the activators of the catalysts.

According to FR 2 521 872 during metathesis lead tetraalkyls can also be added as the activators.

To date organoaluminum compounds have not been recommended as activators. Bosma et al., Journal of Organometallic Chemistry, Vol. 255 (1983), pp. 159–71, did test a number of organometallic compounds and, in so doing, also $(CH_3)_3Al_2Cl_3$, but it was found that the activating effect of this organoaluminum compound is very low.

For specific applications of olefinic compounds prepared through olefin metathesis, such as in the pharmaceutical or cosmetic industries, for example, the use of tin and lead alkyls as activators for metathetical catalysts is impractical for physiological reasons. Notably, these organometallic compounds or their successor products may remain in small quantities in the olefinic reaction mixture following the separation of the heterogeneous rhenium oxide contact and, therefore, remain in the final product employed in commerce.

SUMMARY OF THE INVENTION

Accordingly, it is an object of the present invention to provide effective activators for olefin metathesis which are physiologically acceptable.

The above object and others which will become more apparent in view of the following disclosure are provided by a process for the metathesis of olefins or functionalized olefins or both on $Re_2O_7/Al_2O_3$-containing catalysts, which entails effecting said metathesis reaction in the presence of an effective amount of one or more halogen-free organoaluminum compounds as activators.

DESCRIPTION OF THE PREFERRED EMBODIMENTS

The above-described problem is solved by the provision of halogen-free organoaluminum compounds which are added as activators.

Preferably, organoaluminum compounds of the types $AlR_3$, $XAlR_2$ and $X_2AlR$ are used. In so doing, R stands for alkyl having 1 to 8 carbon atoms. X is an alkoxy having 1 to 8 carbon atoms. Examples for the substituent R are methyl, ethyl, propyl, n-butyl, iso-butyl and hexyl. X is, for example, methoxy, ethoxy or n-butoxy.

Other organoaluminum compounds that are preferably added are alkylaluminoxanes of the formula:

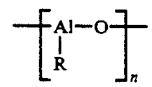

wherein R denotes alkyl having 1 to 8 carbon atoms. Examples thereof are methyl, ethyl, and n-butyl. Methylaluminoxanes are especially preferred. The subscript n has a value in the range of 2 to 30, with from 5 to 20 being preferred.

Alkylaluminoxanes can be manufactured by reacting aluminum trialkyl with water.

During metathesis the organoaluminum compounds can be added in substance or as a solution in an organic solvent. Suitable solvents are anhydrous ethers, hydrocarbons and halogenated hydrocarbons.

The quantity ratios of catalyst to activator can be described with the molar ratio $Re_2O_7$: aluminum in the organoaluminum compound. This ratio ranges preferably from 1:1 to 1:10.

When the quantity of activator is below the minimum value, the reaction during metathesis clearly declines. When the concentration of activator exceeds the maximum value cited here, such concentrations can also be adjusted as no further improvement is attained.

During metathesis a $Re_2O_7/Al_2O_3$-containing supported catalysts is used. In so doing, the catalytically active component can comprise only $Re_2O_7$. However, in addition to $Re_2O_7$, other oxides such a $B_2O_3$, $MoO_3$, $WO_3$ or $V_2O_5$ can also be included. The carrier can comprise $Al_2O_3$. However, in addition to $Al_2O_3$, other oxidic components such as $SiO_2$ can also be included. Preferably, a $B_2O_3$-$Re_2O_7/Al_2O_3$-$SiO_2$ catalyst is used.

Linear, branched and also cyclic olefins can be added for metathesis. These compounds can also generally be metathesized without an activator, however, the use of an activator increases the conversion.

Functionalized olefins, as specified by the invention, are unsaturated esters, ethers, halogen and nitrogen compounds, aldehydes, ketones, and derived alcohols and derived carboxylic acids. Preferably unsaturated carboxylates are added.

When functionalized olefins are metathesized, an activator is generally required, since without an activator no reaction takes place. This applies in particular to the metathesis of unsaturated esters.

The metathetical reactions can be performed as homometathesis, as co-methathesis (use of two different olefinic compounds) and in the case of cyclolefins as the substrate as metathetic, ring-opening polymerization. The metathetical reactions are carried out preferably at room temperature, a state that is advantageous for reasons relating to energy conservation. However, the use of lower or higher temperatures is also possible.

The process to metathesize olefins and functionalized olefins according to the invention makes high conversions and the formation of new products with higher selectivity possible. After separating off the catalyst, the products are free of poisonous lead and tin compounds, which have been conventionally used as activators for the metathesis of functionalized olefins. Therefore, the products are physiologically safe.

The present invention will now be further illustrated by reference to certain Examples which are provided solely for purposes of illustration and are not intended to be limitative.

EXAMPLE 1

Co-methathesis of Oleic Acid Methyl Ester with 4-Octene

Catalyst: $B_2O_3$-$Re_2O_7$/$Al_2O_3$-$SiO_2$, activated with Methylaluminoxane A $B_2O_3$-$Re_2O_7$/$Al_2O_3$-$SiO_2$ supported catalyst is used as the catalyst. The substrate is a powdery, amorphous aluminosilicate with 40 percent by weight of $SiO_2$. The catalyst contains 5.8 percent by weight of $B_2O_3$ and 4.4 percent by weight of $Re_2O_7$, based on the aluminosilicate carrier respectively.

A 9.5% methylaluminoxane solution in toluene is added as the activator. The activator compound has the formula:

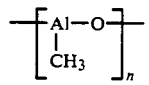

In the above formula, n has a value of about 15, and the average molecular weight is about 900.

In a 50 ml cylindrical shaker flask filled with $N_2$ and comprising magnetic stirring cores, 0.58 g of $B_2O_3$-$Re_2O_7$/$Al_2O_3$-$SiO_2$ catalyst (with 0.053 mmol $Re_2O_7$) are introduced. Then 0.11 ml of methylaluminoxane solution (0.212 mmol Al) and 1 ml of n-heptane are added, where the supported contact becomes dark-brown.

The 4.1 ml of 4-octene (26 mmol) and 4.25 ml of oleic acid methyl ester (13 mmol) are added, where a molar ratio of the individual components is also follows: $Re_2O_7$: Al: oleic acid methyl ester: 4-octene = 1: 4: 250: 500. Thus, Al is the aluminum in the organoaluminum compound.

The mixture is stirred for 2 hours at room temperature. The powdery supported catalyst is left to settle. Of the remaining solution a sample is taken that is analyzed gas chromatographically following the addition of a few drops of methanol to decompose any catalyst residues. According to the reaction equation:

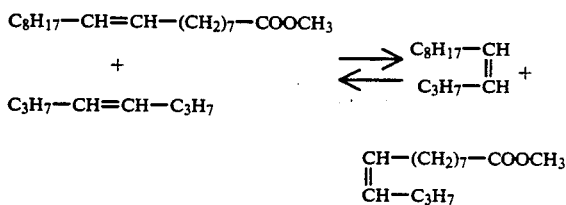

the reaction mixture contains, in addition to the feedstocks, 4-tridecene and 9-tridecenoic acid methyl ester. The conversion of the added oleic acid methyl ester amounts to 56%; the selectivity to metathetical products, 88%.

EXAMPLE 2

The experiment from Example 1 is repeated. In so doing, however, about three times the quantity of catalyst and activator is added. Now the molar ratio of $Re_2O_7$: Al: oleic acid methyl ester: 4-octene = 1:4:80:160. A 78% conversion of oleic acid methyl ester at a selectivity of 89% is obtained.

EXAMPLE 3

Co-metathesis of 10-undecenoic acid methyl ester with 4-octene

Catalyst: $B_2O_3$-$Re_2O_7$/$Al_2O_3$-$SiO_2$, activated with methylaluminoxane The experiment from Example 1 is repeated, wherein, however, oleic acid methyl ester is replaced with 10-undecenoic acid methyl ester. According to the reaction equation

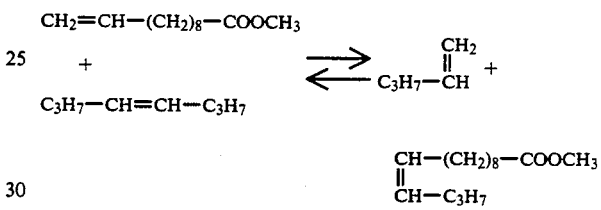

the reaction mixture contains, in addition to the feedstocks, 1-pentene and 10-tetradecenoic acid methyl ester.

. At a molar ratio of $Re_2O_7$: Al: 10 undecenoic acid methyl ester = 1:4:2:250:500, a conversion of 61% with a selectivity of 84% is obtained.

EXAMPLE 4

The experiment from Example 3 is repeated, wherein, however, three times the quantity of catalyst and activator is added. In so doing, the molar ratio of $Re_2O_7$: Al: 10-undecenoic acid methyl ester: 4-octene = 1: 4: 80: 160. The conversion of 10-undecenoic acid methyl ester increases to 81% with a selectivity for the metathesis products of 87%.

EXAMPLE 5

Co-metathesis of 10-undecenoic acid methyl ester with 4-octene

Catalyst: $Re_2O_7$/$Al_2O_3$-$SiO_2$, activate with methylaluminoxane

The experiment from Example 3 is repeated, but now the rhenium oxide supported catalyst contains no $B_2O_3$.

At a molar ratio of $Re_2O_7$: Al: 10-undecenoic acid methyl ester: 4-octene = 1:4:250:500, the conversion of undecenoic acid methyl ester is now 44% with a selectivity of 82%.

EXAMPLE 6

Co-metathesis of 10-undecenoic acid methyl ester with 4-octene

Catalyst: $MoO_3$-$Re_2O_7$/$Al_2O_3$, activated with methylaluminoxane

The experiment from Example 3 is repeated, but now $MoO_3$-$Re_2O_7$ on $Al_2O_3$ is added as the rhenium supported catalyst, which contains 5 percent by weight of $MoO_3$ and 3.5 percent by weight of $Re_2O_7$, based on the support respectively. In addition, about five times the quantity of catalyst and activator is added as compared to Example 3.

At a molar ratio of $Re_2O_7$:Al: 10-undecenoic acid methyl ester: 4-octene = 1:5:50:100, the conversion of 10-undecenoic acid methyl ester is now 20%.

EXAMPLE 7

Co-metathesis of 10-Undecenoic Acid Methyl Ester with 4-Octene Catalyst: $B_2O_3$-$Re_2O_7$/$Al_2O_3$-$SiO_2$, Activated with an Organoaluminum Compound The experiment from Example 3 is repeated. In so doing, however, methylaluminoxane is replaced with an organoaluminum compound according to Table 1.

At a molar ratio of $Re_2O_7$: Al : 10-undecenoic acid methyl ester: 4-octene = 1:4:80:160, the following conversion of undecenoic acid is achieved.

TABLE 1

| Experiment | Activator | Conversion |
|---|---|---|
| a | $Al(C_2H_5)_3$ | 84% |
| b | $Al(i-C_4H_9)_3$ | 84% |
| c | $C_2H_5Al(OC_2H_5)_2$ | 48% |

EXAMPLE 8

Co-metathesis of 4-Octene with 5-Decene

Catalyst: $B_2O_3$-$Re_2O_7$/$Al_2O_3$-$SiO_2$, Activated with Methylaluminoxane In a 50 ml cylindrical shaker flask filled with $N_2$ and comprising magnetic stirring cores, 1.08 g of $B_2O_3$-$Re_2O_7$/$Al_2O_3$-$SiO_2$ supported catalyst (0.098 mmol $Re_2O_7$) described in Example 1 are introduced and treated with 0.21 ml of methylaluminoxane solution (0.392 mmol Al) described in Example 1 and with 23.5 ml of an equimolar mixture of 4-octene and 5-decene, where a molar ratio of the individual components is as follows: $Re_2O_7$: Al: 4-octene: 5-decene = 1:4:800:800.

The mixture is stirred for 2 hours at room temperature. The powdery supported catalyst is left to settle. Of the remaining solution a sample is taken that is analyzed by means of gas chromatography following the addition of a few drops of methanol to decompose any residues of the catalyst. According to the reaction equation:

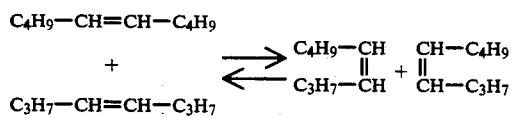

the reaction mixture contains, in addition to the feedstocks, 4-nonene. The conversion of the added olefins amounts of 50%; the selectivity to 4-nonene, 97.6%.

EXAMPLE 9

Co-metathesis of 4-Octene with 5-Decene

Catalyst: $Re_2O_7$/$Al_2O_3$-$SiO_2$, activated with methylaluminoxane

The experiment from Example 8 is repeated, but now the rhenium supported catalyst contains no $B_2O_3$. In addition, the concentration of catalyst and activator is doubled.

At a molar ratio of $Re_2O_7$: Al: 4-octene: 5-decene = 1:400:400, the conversion of olefin amounts to 51% with a selectivity to 4-nonene of 96%.

EXAMPLE 10

Homo-metathesis of 1-octene

Catalyst: $B_2O_3$-$Re_2O_7$/$Al_2O_3$-$SiO_2$, activated with methylaluminoxane The experiment from Example 8 is repeated, however instead of 4-octene/5-decene, 1-octene is added now.

At a molar ratio of $Re_2O_7$: Al: 1-octene = 1:4:1,600, the conversion of 1-octene is 86%. The reaction product is a mixture comprising more than 10 olefins.

EXAMPLE 11

Homo-metathesis of 1-octene

Catalyst: $Re_2O_7$/$Al_2O_3$-$SiO_2$, activated with methylaluminoxane

The experiment from Example 10 is repeated, but now the rhenium supported catalyst contains no $B_2O_3$.

At a molar ratio of $Re_2O_7$: Al: 1-octene = 1:4:800, the conversion of 1-octene is 90%. The reaction mixture is a mixture comprising more than 10 olefins.

EXAMPLE 12

Co-metathesis of 10-undecenoic acid methyl ester with 4-octene

Catalyst: $B_2O_3$-$Re_2O_7$/$Al_2O_3$-$SiO_2$, activated with tetraethyl dialuminoxane The experiment from Example 3 is repeated. In so doing, however, methylaluminoxane is replaced with tetraethyl dialuminoxane (20% in hexane, Al content = 5.9 percent by weight).

At a molar ratio of $Re_2O_7$: Al: 10-undecenoic acid methyl ester: 4-octene = 1: 5.7: 340: 680, the conversion of 10-undecenoic acid methyl ester amounts to 45% with a selectivity of 98%.

EXAMPLE 13

The experiment from Example 12 is repeated, wherein, however, about one and one-half the quantity of catalyst and activator is added. In so doing, the molar ratio of $Re_2O_7$: Al: 10-undecenoic acid methyl ester: 4-octene = 1: 5.7: 230: 460. The conversion of 10-undecenoic acid methyl ester increases to 77% with a selectivity of 87%

EXAMPLE 14

Co-metathesis of 10-Undecenoic Acid Methyl Ester with 4-Octene

Catalyst: $B_2O_3$-$Re_2O_7$/$Al_2O_3$-$SiO_2$, activated with tetraisobutyl dialuminoxane The experiment from Example 3 is repeated. In so doing, however, methylaluminoxane is replaced with tetraisobutyl dialuminoxane (20% in heptane, Al content = 3.6 percent by weight).

At a molar ratio of $Re_2O_7$: Al: 10-undecenoic acid methyl ester: 4-octene = 1: 5.7: 340: 680, the conversion of 10-undecenoic acid methyl ester amounts to 39% with a selectivity of 98%.

EXAMPLE 15

The experiment from Example 14 is repeated, wherein, however, about one and one-half the quantity of catalyst and activator is added. In so doing, the molar ratio of $Re_2O_7$: Al: 10-undecenoic acid methyl ester: 4-octene=1: 5.7: 230: 460. The conversion of 10-undecenoic acid methyl ester increases to 56% with a selectivity of 94%.

Having described the present invention, it will be apparent to one skilled in the art that many changes and modifications may be made to the above-described embodiments without departing from the spirit and scope of the present invention.

What is claimed as new and desired to be secured by Letters Patent of the United States is:

1. In a process for the metathesis of olefins and functionalized olefins on $Re_2O_7/Al_2O_3$-containing catalysts, the improvement which comprises effecting said metathesis reaction in the further presence of $B_2O_3$, $MoO_3$, $WO_3$ or $V_2O_5$, and of one or more halogen-free organoaluminum compounds as activators, wherein said organoaluminum compounds have the formula $X_{(3-M)}AlR_M$ or

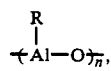

wherein
R is alkyl having 1 to 8 carbon atoms,
X is alkoxy having 1 to 8 carbon atoms,
M is 1 or 2, and
n is 2 to 30.

2. The process of claim 1, wherein said organoaluminum compounds have the formula $X_{(3-M)}AlR_M$, wherein
R is alkyl having 1 to 8 carbon atoms,
X is alkoxy having 1 to 8 carbon atoms, and
M is 1 or 2.

3. The process of claim 1, wherein said organoaluminum compounds are of the formula:

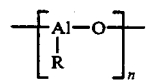

wherein
R is alkyl having 1 to 8 carbon atoms, and
n is 2 to 30.

4. The process of claim 3, wherein in said organoaluminum compounds n is a number ranging from 5 to 20.

5. The process of claim 1, wherein the molar ratio $Re_2O_7$: aluminum in the organoaluminum compound ranges from 1:1 to 1:10.

6. The process of claim 1, wherein the functionalized olefins are unsaturated carboxylic acid esters.

7. The process of claim 2, wherein R is methyl, ethyl, propyl, n-butyl, iso-butyl or hexyl.

8. The process of claim 2, wherein X is methoxy, ethoxy or n-butoxy.

9. The process of claim 1, wherein said catalyst contains a compound of the formula $B_2O_3$-$Re_2O_7$/$Al_2O_3$-$SiO_2$.

10. The process of claim 1, wherein the functionalized olefins are unsaturated esters, ethers, halogen or nitrogen compounds, aldehydes, ketones or derived alcohols or derived carboxylic acids.

11. The process of claim 1, wherein the process is a co-metathesis of oleic acid methyl ester with 4-octene.

12. The process of claim 1, wherein the process is a co-metathesis of 10-undecenoic acid methyl ester with 4-octene.

13. The process of claim 1, wherein the process is a co-metathesis of 4-octene with 5-decene.

14. The process of claim 1, wherein the process is a homo-metathesis of 1-octene.

* * * * *